(12) United States Patent
Pourcelot et al.

(10) Patent No.: US 7,010,435 B2
(45) Date of Patent: Mar. 7, 2006

(54) METHOD FOR MEASURING TENSION STATE OF A MATERIAL AND USES THEREOF

(75) Inventors: Philippe Pourcelot, Veigne (FR); Nathalie Crevier-Denoix, Joinville le Pont (FR); Berangere Ravary, Maisons Alfort (FR)

(73) Assignee: Institut National de la Recherche Agronomique (INRA), Paris Cedex (FR)

( * ) Notice: Subject to any disclaimer, the term of this patent is extended or adjusted under 35 U.S.C. 154(b) by 0 days.

(21) Appl. No.: 10/492,601

(22) PCT Filed: Oct. 16, 2002

(86) PCT No.: PCT/FR02/03544

§ 371 (c)(1),
(2), (4) Date: Apr. 15, 2004

(87) PCT Pub. No.: WO03/032842

PCT Pub. Date: Apr. 24, 2003

(65) Prior Publication Data
US 2004/0249580 A1  Dec. 9, 2004

(30) Foreign Application Priority Data
Oct. 16, 2001  (FR)  .................................. 01 13327

(51) Int. Cl.
*G01L 1/00* (2006.01)
*G01G 11/00* (2006.01)
*A61B 5/10* (2006.01)

(52) U.S. Cl. ...................... 702/43; 156/73.1; 424/93.1; 600/587; 702/41

(58) Field of Classification Search ............ 702/41–43, 702/142, 152, 173, 175, 187; 600/437, 442, 600/453, 586, 588, 449; 73/379.01, 788, 73/826, 627, 772; 156/73.1; 424/93.1
See application file for complete search history.

(56) References Cited

U.S. PATENT DOCUMENTS

| | | | |
|---|---|---|---|
| 4,993,427 A * | 2/1991 | Barr et al. .................. | 600/587 |
| 5,170,366 A | 12/1992 | Passarelli | |
| 5,678,565 A | 10/1997 | Sarvazyan | |
| 5,685,307 A | 11/1997 | Holland et al. | |
| 6,007,489 A | 12/1999 | Yost et al. | |
| 6,193,658 B1 | 2/2001 | Wendelken et al. | |
| 6,213,934 B1 | 4/2001 | Bianco et al. | |
| 6,562,166 B1 * | 5/2003 | Molander et al. .......... | 156/73.1 |
| 6,878,371 B1 * | 4/2005 | Ueno et al. ................ | 424/93.1 |

FOREIGN PATENT DOCUMENTS

| | | |
|---|---|---|
| EP | 1 079 240 A2 | 2/2001 |
| WO | WO 99 45348 A | 9/1999 |

* cited by examiner

*Primary Examiner*—Michael Nghiem
*Assistant Examiner*—John Le
(74) *Attorney, Agent, or Firm*—Jacobson Holman PLLC

(57) ABSTRACT

A method for determining the state of tension of a material at a given time, including the step of calculating the value of at least one parameter extracted from the ultrasonic signal received after propagation of an ultrasonic wave emitted in the material between an ultrasound source and at least an ultrasound emitter located at a fixed distance from the source, the value of the at least one parameter varying with the state of tension of the material, the variation of the at least one parameter being proportional or inversely proportional to the variation of the state of tension of the material.

22 Claims, 10 Drawing Sheets

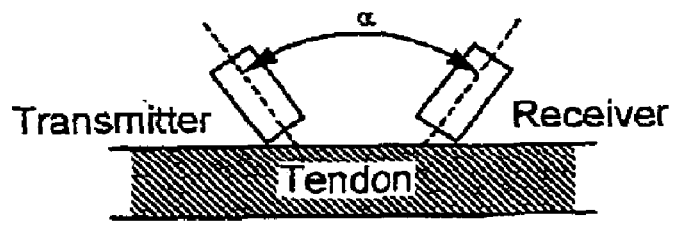
FIGURE 2a: ANGLE CONVENTION USED
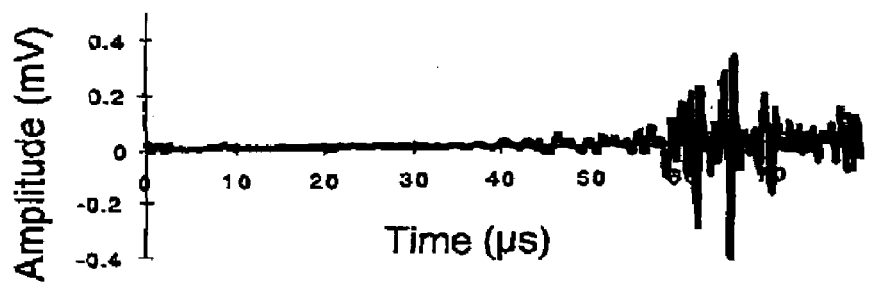
FIGURE 2b: α = 40°
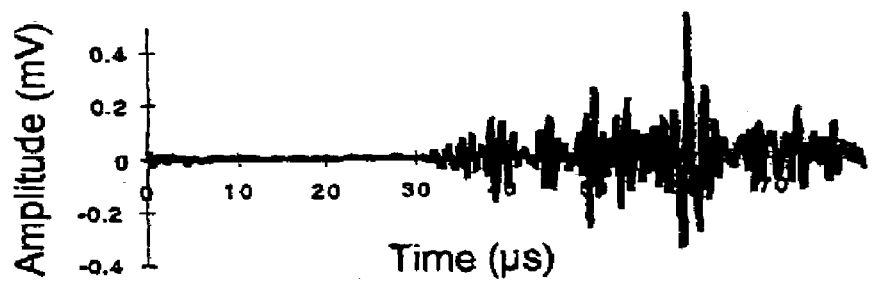
FIGURE 2c: α = 80°
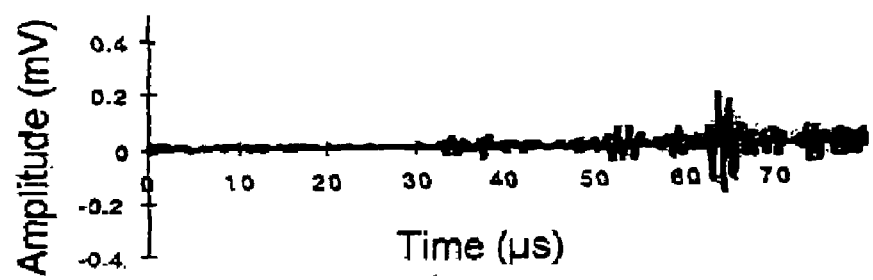
FIGURE 2d: α = 110°

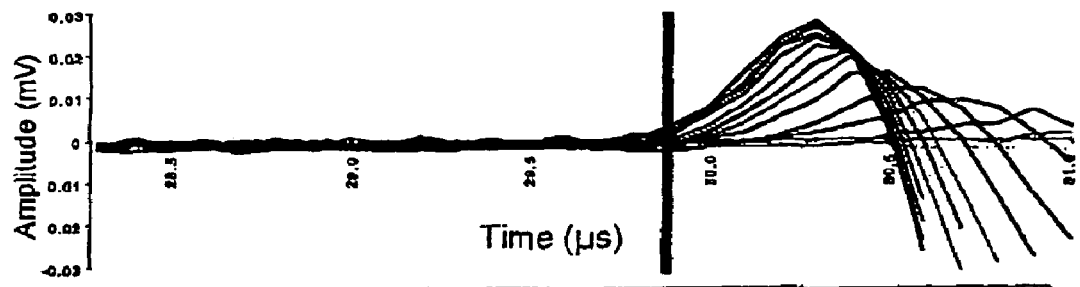
FIGURE 6a: Skin intact
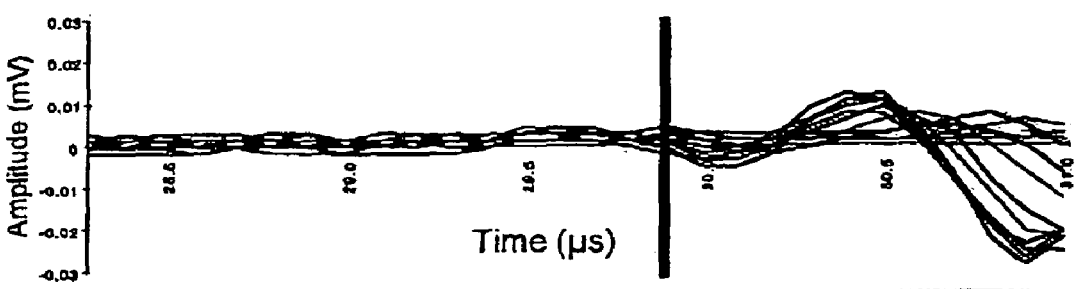
FIGURE 6b: Skin incised
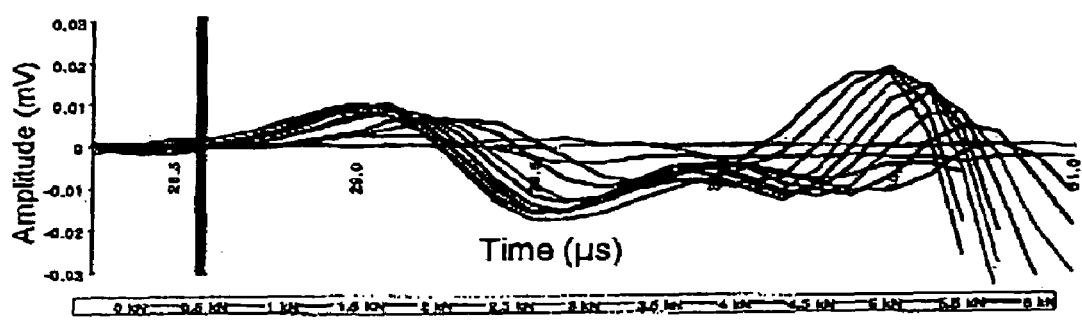
FIGURE 6c: Skin withdrawn
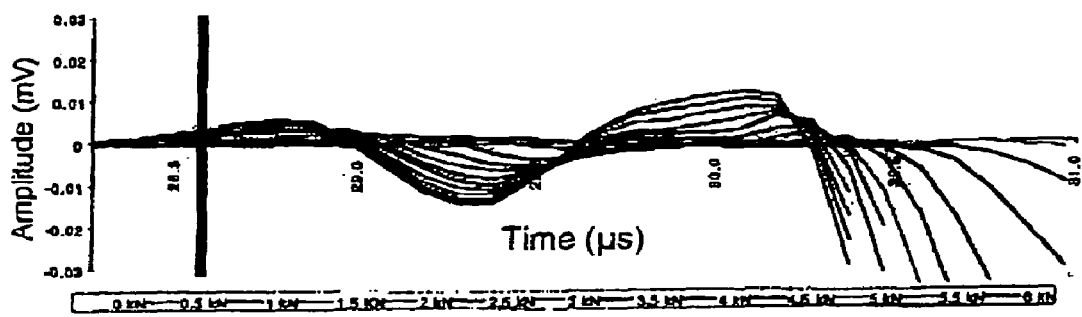
FIGURE 6d: TFSD insulated acoustically — Phase when the lower limb is resting on the ground

METHOD FOR MEASURING TENSION STATE OF A MATERIAL AND USES THEREOF

This is a nationalization of PCT/FR02/03544 filed Oct. 16, 2002 and published in French.

This invention relates to the general measurement of the tension condition of a material, notably of a biological material such as a tendon, a ligament or a muscle.

PREVIOUS ART

The measurement of the tension condition of a material, biological or non-biological, exhibits considerable interest in numerous industrial fields.

It is essential, for numerous mechanical devices, to know the tension condition of their different elements during the different phases of their operation, notably in order to evaluate the capacity of mechanical resistance of these devices during their current usage. Such devices include terrestrial or air vehicles, for which certain parts of composite material are liable to undergo high mechanical loads when in motion.

The determination of the tension condition of a biological material, and more specifically of a tendon, of a ligament or of a muscle in response to mechanical strains exerted statically, in isometric contraction for example, or dynamically, during normal or pathological locomotion or still during different sportive movements or gestures, also provides great technical interest.

In human as in animals, the development of shoes or of irons adapted to the various types of mechanical strains specific to the type of activity, for example running, jumping, could be optimised if the industrialist could benefit from a simple and reproducible measurement for the determination of the tension condition of a tendon, of a ligament or of a muscle at the different movement phases of the subject in the activity considered. The accessibility of such a measurement would enable, for instance, the design of soles, of irons or of palms with optimised mechanical characteristics to practice a particular sport.

Similarly, such a measurement would enable to study or to select corrective devices for walking, running or any other static or dynamic gesture, and this for damaged tendinous, ligamentous or muscular tissues or in rehabilitation phase such as corrective soles in man or corrective iron fittings in equines.

Such a measurement would also contribute to the design of new sportive or medical equipment, such as shoes and irons, palms, ski fasteners, body building equipment.

In vitro studies have enabled to assess the changes and deformations exerted on the tendons of the hand of the horse during the different phases of the stride. One may quote notably the works of Jansen et al. and of Riemersma et al. (Jansen M O et al., In vivo tendon forces in the forelimb of ponies at the walk validated by ground reaction forces measurements, Acta Anatomica, 1993, 146:162–167; Riemersma D J et al., influence of shoeing on ground reaction forces and tendon strains in the forelimb in ponies, Equine Vet. J., 1996, 28(2):126–132; Riemersma D J et al., Tendon strain in the forelimbs as a function of gait and ground characteristics and in vitro limb loading in ponies, Equine Vet. J., 1996, 28(2):133–138; Riemersma D J et al., Kinetics and kinematics of the equine hindleg: II, in vivo tendon strain and joint kinematics, Am. J. Vet. Res., 1988, 49:1353–1359) which use deformation-gauge intra-tendinous transducers or still the works of Stephens et al. (Stephens P R et al., Application of a Hall-effect transducer for measurement of tendon strain in Horses, Am. J. Vet. Res., 1989, 50:1089–1095) using Hall-effect transducers.

It has also been suggested to measure the load exerted on a tendon using optical fibres (Erdemir and al., in vitro evaluation of a fiberoptic transducer for tendon force measurements, Congress of the International Biomechanical Society, Zurich, July 2001).

The invasive or intrusive nature of the transducers used in the state of the art generates not only problems of ethical nature, but also numerous methodological difficulties.

Thus, the implantation of such transducers, which requires general anaesthesia, affects the local mechanical properties of the tendons in a few days only, which biases the measurement rather significantly. Besides, the pain experienced by the animal is such that only measurements at slow paces (step and trot) may generally be realised. Finally, for reasons associated with the calibration of the measurements, the animal must be put down at the end of the experiment. There is therefore a real need in the current state of the art to develop a method which may constitute an << in vivo transducer >> and which enables direct and non-invasive measurement of the tension condition of a tendon, of a ligament or of a muscle. Thus, the implantation of such transducers, which requires general anaesthesia, affects the local mechanical properties of the tendons in a few days only, which biases the measurement rather significantly. Besides, the pain experienced by the animal is such that only measurements at slow paces (step and trot) may generally be realised. Finally, for reasons associated with the calibration of the measurements, the animal must be sacrificed at the end of the experiment. There is therefore a real need in the current state of the art to develop a method which may constitute an << in vivo transducer >> and which enables direct and non-invasive measurement of the tension condition of a tendon, of a ligament or of a muscle.

There is then provided according to the invention a simple and reproducible method of determination of the tension condition of a material, biological or non-biological, based on the calculation of the value of at least one parameter extracted on the basis of the ultrasonic signal received after propagation of an ultrasonic wave in said material.

The ultrasounds have been used for some ten years to characterise biological or non-biological materials. The scanning systems constitute an illustration of the use ultrasounds in medical imaging. For instance, the patent U.S. Pat. No. 6,193,658 issued on 27 Feb. 2001 describes an ultrasound device usable for measuring the extent of a lesion in the soft tissues and the bone, including the tendons, the ligaments and the muscles. Such a device is adapted to the detection and to the measurement of cavernous lesions, after filling the cavernous lesion with a fluid medium before obstruction of the lesion using a film whereon is applied the ultrasound measuring device.

The patent U.S. Pat. No. 5,685,307 delivered on 11 Nov. 1997 describes an ultrasound measuring device of the fat mass on the carcass of an animal.

The Doppler effect has also been utilised to track the heart beat by ultrasound scan analysis, as it is described in the European patent application EP-1 079 240.

Measuring the speed of ultrasounds has also been used to detect micro-fractures or deformations at the bones, to assess the bone density, to evaluate the bone healing process or to measure the thickness of the bone cortex, as described in the PCT application N°WO 99/45 348.

It has also been suggested to measure the travel time of the ultrasounds to evaluate the deformation of a rigid structure relative to the mechanical strains undergone by this rigid structure. Thus, the U.S. Pat. No. 5,170,366 describes a method of measurement using two independent ultrasound transducers, the measurement of the travel time of the ultrasounds enabling to assess the distance between both transducers and thereby to determine the deformation of the rigid material under the effect of a mechanical strain. According to the method described in this patent, both ultrasound transducers are each fixed at a given spot to the rigid material tested, but said transducers are mobile, relative to one another.

To the best of the applicant's knowledge, it has never been suggested to use the ultrasounds in order to measure the tension condition of a material, regardless whether it is biological material or a non-biological material.

DETAILED DESCRIPTION OF THE INVENTION

It has now been shown according to the invention that the tension condition of a material may be determined by the measurement of at least one parameter extracted from the ultrasonic signal received after propagation of an ultrasonic wave in said material.

The object of the invention is a method to determine the tension condition of a material at a given time, comprising one step during which one calculates the value of at least one parameter extracted from the ultrasonic signal received after propagation of an ultrasonic wave transmitted in said material, the value of the parameter(s) varying with the tension condition of the material between an ultrasound source and at least one ultrasound receiver situated at a fixed predetermined distance from said source, said variation of the parameter(s) being proportional or reversely proportional to the variation in the tension condition of said material.

By << tension condition >> of a material, is meant according to the invention, the physical condition which characterises this material, which results from the set of strains, notably mechanical strains (examples: strength, deformation), undergone by said material, at a given time.

According to the invention, the variation of a parameter extracted from the ultrasonic signal is << proportional >> to the variation in the tension condition of the material tested when the value of said parameter increases with the increase of the tension condition of the material and when the value of said parameter decreases with the diminution of the tension condition of the material.

According to the invention, the variation of a parameter extracted from the ultrasonic signal is << reversely proportional >> to the variation in the tension condition of the material tested when the value of said parameter diminishes with the increasing of the tension condition of the material and when the value of said parameter increases with the diminishing of the tension condition of the material.

This does not necessarily mean that the value of the parameter extracted from the ultrasonic signal is a simple multiple of the value of the tension condition of the material. The relation between the value of the parameter extracted from the ultrasonic signal and the value of the tension condition of the material may also consist of a complex mathematic function.

The mathematic function connecting the variation of the parameter extracted from the ultrasonic signal and the variation in the tension condition of the material tested may be determined conventionally by the man of the art.

Moreover, the knowledge of the mathematic function connecting the variation in the value of the parameter extracted from the ultrasonic signal to the variation in the tension condition of the material tested is not necessarily required. For each of the parameters considered, the man of the art may establish a calibration curve with a first axis corresponding to the values of the parameter extracted from the ultrasonic signal and a second axis corresponding to the values of tension condition of the material tested. The calibration curve is built by applying to the material tested a series of mechanical strains of known values, for instance a series of loads of known values, and by measuring, for each point of this mechanical strain the value of the parameter extracted from the sound signal. Then, to evaluate the tension condition of the material tested, at a given time, one measures the value of the parameter extracted from the ultrasonic signal and the one carries this measurement over to the pre-established calibration curve in order to determine the value of the mechanical strain (for example the load) of the material tested at this given instant.

Alternately, the quantitative determination of the value of the tension condition of the material tested, at a given time, is not always required. In numerous situations, what is important is the determination of the variation in the tension condition of said material between two measurement instants or between two distinct conditions of measurement and therefore simply the comparison of the value of tension obtained, between these two instants, by measuring at each of both times or for each of both conditions of measurement of the value of the parameter extracted from the ultrasound signal.

The method above is characterised in that the parameter(s) calculated on the basis of the ultrasonic signal received after propagation of the ultrasonic wave in the material is (are) selected(s) among the following parameters:
  (i) the travel time of the ultrasonic wave over a predetermined distance in said material;
  (ii) the amplitude of the ultrasonic wave at the reception point of the ultrasonic signal;
  (iii) the attenuation of the ultrasonic wave at the reception point of the ultrasonic signal;
  (iv) the average frequency of the ultrasonic wave at the reception point of the ultrasonic signal;
  (v) the maximum frequency of the ultrasonic wave at the reception point of the ultrasound signal.

It has been shown in particular according to the invention that the travel time, the amplitude and the attenuation of the ultrasounds travelling through a tissue of the tendon, ligament or muscle type, vary depending on the tension condition of this tissue.

More specifically, it has been shown according to the invention that the amplitude of an ultrasonic wave in a tendinous, ligamentous or muscular tissue increases relative to the tension load exerted on the tissue considered. It has also been shown that the travel time and the attenuation of the ultrasonic wave decrease relative to this same load. This latter characteristic has been shown notably for man and for horse.

The applicant has also observed that the average frequency and the maximum frequency of the ultrasonic wave vary relative to the tension condition of the material, notably of the tendon, of the ligament or of the muscle.

Without willing to be bound by any particular theory, the applicant thinks that the variations in the travel time, the amplitude, the attenuation, the average frequency and the maximum frequency of an ultrasonic wave may also be observed for non-biological materials, and more specifically on non-biological materials whereof the physical structure comes closer to that of a tendon, of a ligament or of a muscle, i.e. on the non-biological materials having a structure constituted of fibres oriented according to a main axis. This applies in particular to the non-biological materials constituted of fibres included in a matrix, as in the composite materials.

Among the non-biological materials preferred, the composite materials composed of carbon fibres, of glass fibres or of Kevlar® fibres are notably preferred.

Building up on these observations, the applicant has developed a method to determine the tension condition of a tendon, of a ligament or of a muscle by measuring, or by measuring and calculating, at least one parameter.

Preferably, the parameters extracted from the ultrasonic signal is (are) selected(s) among (i) the travel time of the ultrasonic wave over a predetermined distance from said tissue, (ii) the amplitude of the ultrasonic wave at the reception point of the ultrasound signal, (iii) the attenuation, (iv) the average frequency and (v) the maximum frequency of the ultrasonic signal at the reception point of the ultrasounds.

The invention also relates to a method to determine the tension condition of a tendon, of a ligament or of a muscle at a given time comprising one step during which one calculates the travel time or the amplitude or the attenuation of an ultrasonic wave in the tissue of said tendon, of said ligament or of said muscle, the travel time, the amplitude and the attenuation depending on the tension load of said tendon, of said ligament or of said muscle at this given instant.

Advantageously, the method according to the invention may be carried out by calculating the value of a plurality of parameters extracted from the ultrasound signal, preferably a plurality of parameters among those listed previously.

Preferably, the method according to the invention is characterised in that one calculates the parameter values for at least one of the following combinations of parameters:
  (i) the travel time and the amplitude of the ultrasonic wave;
  (ii) the travel time and the attenuation of the ultrasonic wave;
  (iii) the amplitude and the attenuation of the ultrasonic wave;
  (iv) the travel time, the amplitude and the attenuation of the ultrasonic wave.

Preferably, the method according to the invention is characterised in that one calculates the values of parameter for at least one of the following combinations of parameters:
  (i) the travel time and the amplitude of the ultrasonic wave;
  (ii) the travel time and the attenuation of the ultrasonic wave;
  (iii) the amplitude and the attenuation of the ultrasonic wave;
  (iv) the travel time, the amplitude and the attenuation of the ultrasonic wave.

Contrary to the methods of the state of the art, the method above enables to determine the tension condition of a tendon, of a ligament or of a muscle without any invasive step such as implanting measuring materials, like deformation gauges, Hall-effect transducers or still optical fibres.

Similarly, for the non-biological materials, the method of the invention enables to perform measurements of the tension condition of the material, for instance an airplane part, without altering its structure. After measurement, the material, for instance the airplane part, may be re-used normally in its primary condition.

According to the method, one applies a transmitter ultrasound transducer in contact with the material to be treated, then the signals from this transmitter and which have travelled said material over a predetermined length or distance, are received by dint of one or of several receiver ultrasound transducers.

When the method is carried out on a biological material of the tendon, ligament or muscle type, one applies a transmitter ultrasound transducer in contact with the skin, facing the tendon, the ligament or the muscle for which the measurement of the tension condition is requested, then the signals from this transmitter are received by dint of one or of several receiver ultrasound transducers.

It has been shown according to the invention that the measurement of the variations of travel time, amplitude or attenuation of the ultrasounds relative to the tension load of the tendon, of the ligament or of the muscle is not altered according to that the transmission and reception points of the ultrasounds are applied directly to the tendon, the ligament or the muscle, or simply brought into contact with the overlying skin.

The ultrasounds passing through the skin and the conjunctive tissues of the tendon, of the ligament or of the muscle, do not affect the measurement of the variations in travel time, amplitude or attenuation of the ultrasounds.

Consequently, the method according to the invention does not require any complex system for correcting the measurement taking into account the path of the ultrasound beam through the skin or the conjunctive tissues surrounding the tissue whereof the tension load is measured.

The invention relates to a method to determine the tension condition of a material at a given time, characterised in that it comprises the following steps:
  a) application of an ultrasound source in contact with the material to be tested and record the signals from this ultrasound source after propagation in said material using at least one receiver situated at a fixed predetermined distance from said source, the line connecting the source and the receivers being parallel to the longitudinal axis of the material to be tested.
  b) determination of the tension condition of the material by calculating the value of the parameter(s) extracted from the ultrasonic signal at a given time.

According to an advantageous characteristic of the method, the ultrasound source and the ultrasound receivers are placed in contact with the material to be tested and aligned according to the main axis of said material, generally the longitudinal axis of said material.

The longitudinal axis of the material to be tested is the main orientation axis of the fibres forming said material.

The invention also relates to a method to determine the tension condition of a tendon, a ligament or a muscle, said method comprising the following steps:
  a) application of an ultrasound source in contact with the skin facing a tendon, a ligament or a muscle and reception of the signals from this ultrasound source after propagation in said material using at least one receiver situated at a fixed, predetermined distance of said source, the source and the receivers being aligned according to the main axis of the tendon, of the ligament or of the muscle under investigation,
  b) determination of the tension condition of the tendon, of the ligament or of the muscle by calculating the value of the parameters extracted from the ultrasonic signal at a given time.

Preferably, the ultrasound source and the receivers enabling the reception of the signals from the ultrasound source consist of conventional ultrasound transducers, respectively a transducer transmitter and one or several transducer receivers well-known in the state of the art.

According to an advantageous characteristic of the method, the ultrasound source and the ultrasound receivers are placed in contact with the material to be tested and aligned according to the main axis of said material.

According to an advantageous characteristic of the method above, the ultrasound source and the ultrasound receivers are placed on the skin according to the main axis of the tissue investigated, the receivers being situated at a fixed predetermined distance from the ultrasound transmission source. According to this advantageous characteristic, the distance to be travelled by the ultrasounds is constant with the course of time when a succession of measurements is performed, the single variable parameter being then the tension condition of the tissue investigated.

According to another advantageous characteristic of the method above, the axis whereon are placed the ultrasound transmission source and the receiver(s) is the main axis of the tissue investigated, i.e. the axis along which are aligned the tendinous, ligamentous or muscular fibres. According to this characteristic, one avoids the measurement of artefacts which might have resulted from a path of the ultrasounds imposed by a placement of transducers perpendicular to the axis of the tendinous, ligamentous or muscular fibres, artefacts associated with the variations in diameter of the tissue considered (tendon, ligament or muscle) according to the tension load applied to said tissue, notably during muscular contractions or the elongation of the tendons or of the ligaments.

As illustrated in the examples, correlations have been established between the tension load applied to the tendon and the travel time, the amplitude and the attenuation of the ultrasonic wave in the tissue thereof. As the tension load applied to the tendon increases, the amplitude also increases whereas the travel time and the attenuation of the ultrasonic signal diminish.

According to a preferred embodiment of the method, the signals from the ultrasound source are received by a plurality of receivers situated at a predetermined distance with respect to the source.

According to this embodiment, the ultrasound source and the plurality of receivers are aligned according to the axis of the tendinous, ligamentous or muscular fibres.

Advantageously, the ultrasound source and the receivers are included in the same box, which enables to maintain constant in the long-run the distance from the transmitter to the receivers as the distances separating the receivers.

According still to another embodiment complying with the invention, said box comprises a plurality of ultrasound transmitters, the transmitters being arranged, for instance in the box above, according to an axis perpendicular to the axis formed by the alignment of the transmitter and of the receiver or the plurality of receivers as described previously. In this particular embodiment, each transmitter is aligned with a receiver or a plurality of receivers, the axes formed by the alignment of a transmitter given and of the corresponding receiver(s) being parallel to one another and perpendicular to the axis formed by the alignment of the transmitters. According to this embodiment, the transmitters and the receivers are arranged according to a matrix, as described for instance in the PCT international application published on 10 Sep. 1999 under the number WO 99/45348.

Thanks to such a device, it is possible to select, when measuring, the transmitter and the receivers aligned with the latter which enable to receive an optimal signal, which enables to remedy possible malfunctions caused by the displacement of the device over the surface of the material to be tested during the measurement, for instance when measuring the tension condition of a tendon of a man or of a animal during the race.

Preferably, the device comprising a transmitter and one or a plurality of receivers is connected to an electronic box for controlling and processing the ultrasound signal. This electronic box may be itself connected to a digital computer whereof the memory has been loaded previously with a computer programme able to manage the transmission of the ultrasounds and the storage of the signals captured.

The travel time of the ultrasounds along the main axis of the material to be tested, notably along the main axis of the tendon, of the ligament or of the muscle, may be represented as the travel time of the ultrasonic wave between the transmitter and one at least of the receivers.

According to another aspect, the travel time of the ultrasonic wave may be represented as the travel time of the signal between at least two receivers selected among the plurality of receivers. According to this particular aspect, the measurement accuracy is the greater since the number of receivers between which the travel time of the ultrasounds is measured is large. Thus, when the measuring device comprises five receivers $R_1$ to $R_5$, as illustrated in FIGS. 7A and 7B, the travel time of the ultrasonic wave between the receivers $R_1$ and $R_5$ may be measured, then expressed relative to the distance between these transducers.

In this embodiment, one measures the travel time of the ultrasounds successively between the receiver $R_1$ and the other receivers, i.e. successively between $R_1$ and $R_2$, $R_1$ and $R_3$, $R_1$ and $R_4$, $R_1$ and $R_5$.

If one expresses these measurements in the form of a curve whereof the abscissa is the travel time measured between $R_1$ and each of the other four receivers and the ordinate the distance between $R_1$ and each of the other four receivers, then the slope of the curve thereby obtained is the greater since the celerity of the ultrasounds is high.

In order to measure the variation in travel time of the ultrasounds relative to the tension condition of the tissue investigated, another method than that describe above may be employed. Since the plot of the signals acquired for increasing or decreasing loads exhibits progressive evolution simultaneously in their phase and in their amplitude, this method consists in calculating the time-lag (backward or forward) between two signals recorded successively while determining the maximum of the intercorrelation function of both these signals on a given time window.

The time window whereon takes place the intercorrelation may vary from 1 to 50 microseconds, preferably 2 to 10 microseconds for an ultrasound transmission at 1 MHz.

To determine the maximum of the intercorrelation function of both these signals on a given time window, the man of the art may advantageously refer to the book of M. KUNT (1981, << Digital processing of signals>> DUNOD Ed., pp. 16–17 and 57).

To break away from time resolution associated with the sampling frequency of the ultrasound signals, one performs an interpolation of the maximum of the intercorrelation function, for instance by Fast Fourier Transform (book of M. Kunt, 1981, << Digital processing of signals>> DUNOD Ed., pp. 173–174) or by parabolic interpolation (book of F. SCHEID, 1986, << Digital analysis >> Series Schaum, Mc Gray Hill Ed., pp 82–87 and 90–99) on the base of the 3 points defining the maximum.

As the travel time, the amplitude and the attenuation of the ultrasonic wave depend on the load exerted on the tendon, the ligament or the muscle. The ultrasonic wave received by the ultrasound transducer(s) is a complex signal composed of a summation of waves whereof the amplitudes and the frequencies are distinct. It has been shown according to the invention that, for a load applied to the material to be tested, for instance a tendon, the ultrasonic signal received by the transducers may be characterised notably by a value of amplitude, of attenuation and of frequency.

The amplitude of the ultrasonic signal may be represented as the maximum value of the module of the Fourier transform of this signal, which may be calculated by the man of the art, notably complying with the teaching of the book of M. KUNT (1981, << Digital processing of the signals>> DUNOD Ed., pp. 133 and 165–170).

The attenuation of the ultrasonic signal may be represented as the slope of the attenuation function (in dB/MHz) obtained by reporting the modules of the frequency spectra to the modules taken as reference. The reference modules may, for instance, be those calculated for the highest load applied.

The frequency of the ultrasonic signal may be, notably, characterised by two parameters. The maximum frequency may be represented as the frequency corresponding to the maximum amplitude of the module of the frequency spectrum and the average frequency as the barycentre of the frequency spectrum.

The amplitude of the ultrasonic wave is the higher since the load exerted on the tissue investigated is great. Reversely, the attenuation of the ultrasonic wave is the lower since the load exerted on the tissue investigated is great.

To calculate the frequency spectrum and the amplitude spectrum, the man of the art may advantageously refer to the book of M. KUNT (1981, << Digital processing of signals>>, DUNOD Ed., pp. 12–13).

According still to another aspect of the method of the invention, the applicant has shown that the angle between the transmitter and the receivers had a significant incidence, notably on the amplitude of the ultrasonic wave and has consequently a significant influence on the accuracy of the measurements.

Although the angle between the ultrasound transmitter, on the one hand, and the ultrasound receiver(s), on the other hand, may vary from 0° to 180° and that the optimum angle depends notably of the material or of the biological tissue investigated, on its acoustic impedance, its thickness or still the number of layers to go through before reaching it, it has been shown according to the invention that, to carry out measurements on the surface tendon of the finger of the horse, the optimum operating conditions were reached when that angle ranged between 20° and 160°.

Quite preferably, the angle formed between the ultrasound transmitter and the receivers ranges between 60° and 100° and still more preferably is approximately 80°.

Advantageously, the frequency of ultrasounds transmitted by the source ranges between 15 KHz and 10 GHz, preferably between 20 KHz and 100 MHz, and quite preferably between 20 KHz and 50 MHz.

Preferably, the method according to the invention is characterised in that the parameter(s) extracted from the ultrasonic signal received is (are) calculated between at least two receivers.

By repeating the above method for a plurality of given instants, the tension condition of a material to be tested, notably of a tendon, of a ligament or of a muscle, may be measured continuously on the material in the conditions of its use or of its operation, for instance on a man or an animal in motion or not, in order to track in real time the tension loads imposed on the material or the biological tissue tested.

The invention also relates to a method for continuous measurement of the tension condition of a material, characterised in that one implements the method of determination of the tension condition of a material as defined previously, for a plurality of time-spread, given instants.

When the material to be tested is a tendon, a ligament or a muscle, the above method may be implemented in various situations of movement of a man or an animal, notably the locomotion (walking, trotting, galloping, racing, jumping, swimming), in all the pace phases (dampening, propulsion, bringing limbs back, spreading limbs, take-off) or any static situation or dynamic movement.

Preferably, the frequency of measurement of the tension condition of the tissue investigated is greater than or equal to 2.5 times that of the frequency at which evolves the tension condition.

For illustrative purposes, the complete cycle of a limb, i.e. the stride of a horse trotting leisurely at a speed of 3 to 4 meters per second, is realised, in average, in 0.68 second, the back-up phase during approximately 0.34 second.

If it is assessed that during this back-up phase the maximum frequency at which the tension of the tendon to be investigated evolves is 40 Hz, 100 measurements per second will have to be carried out to determine the tension condition of this tendon during the back-up phase.

The above method may be applied to the determination of the tension condition of a tendon, of a muscle or of a ligament, in a man or an animal at a given time, or to tracking the variations in the tension condition of the tissue biological considered in the course of time, for instance during a locomotion (walking or racing), normal or pathological, or still during a sportive action.

In particular, the method according to the invention may be realised on damaged tissues, for instance in the case of inflammation or other lesions of the tendons, or still after fitting a limb with a prosthesis.

In a man, the above method may be implemented, for instance, to determine the tension condition of certain tendons, as the Achilles' tendon, the tendon of the triceps brachial or still the knee-joint tendon or patellar ligament.

The implementation of the method according to the invention on human or animal tissues enables to measure directly the strains exerted on different anatomic formations, for instance the loads to which are subjected the tendons, the ligaments and the muscles in diverse circumstances, i.e. during a normal locomotion or a pathological locomotion or still during different gestures (notably sportive gestures), regardless whether on healthy tissues, damaged tissues or still after fitting the limbs with prostheses.

The implementation of the method according to invention may be carried out during clinical tests, valuations of the efficiency of certain chemical, mechanical rehabilitation therapies.

It may also be useful when designing new sportive, rehabilitation or medical material, such as sport shoes, diving palms, ski fasteners, body building apparatus.

The method according to the invention may also be applied to the characterisation of the lesions of a tendon, of a ligament or of a muscle or still to the determination of the extent of such lesions.

For illustrative purposes, the method for continuous measurement of the tension condition of a tendon, of a muscle or of a ligament defined above may be applied to racing horses. Indeed, the tendons are formations whereof the architecture is highly specialised and adapted to tensile resistance. Any lesion involves a loss of this organisation and the healing process, particularly slow, is generally incomplete and does not enable the tendon to recover its original structural and mechanical properties. The mechanical properties of a damaged tendon evolve with the healing. For a recent lesion, the tendon—in spite of its increased section—is brittle and may be deformed. When the lesion is old, the residual hypertrophy, associated with greater rigidity, makes comparatively more brittle the segments adjoining the initial lesion, at the level of which relapses generally take place. In the healing phase, the horses are classically fitted with corrective orthopaedic iron fittings which should be adapted to limit the tension loads of the tendon healing further to their effects on the digital joint configurations. In order to promote the speed and the degree of healing, the following principles should be observed preferably:

1) During the first phase, i.e. during the first four to six weeks of evolution of the tendinous lesion, it is advisable to select a corrective iron fitting capable of relieving at most the tendon reached by reducing the tension undergone by the tendon, to avoid any aggravation and promote the healing process;
2) Then, during the following phase, extending from the second to the fourth month approximately, it is preferable to try and stress the tendon slightly in order (i) to promote longitudinal re-alignment of the fibres and (ii) to avoid healing retractions. It will be judicious to select an iron fitting capable of inducing gradual elongation of the tendon, as the healing process progresses, in order to improve the deformability of the healing tissue. The final object is to reduce the risks of later relapse since short and thick segments predispose the tendon to relapses at the junction between healthy tissues and damaged tissues;
3) Finally, when resuming the sportive activity, generally after a period of 4 to 6 months after lesion, it is necessary to select an iron fitting capable of sparing the tendon as far as possible, which is most subjected to relapses at this stage.

The method for continuous measurement of the tension condition of a tendon, of a muscle or of a ligament according to the invention, when applied to equines, is preferably implemented to determine the tension condition of the superficial flexional tendon of the finger (TFSD) or of its accessory ligament (LA-TFSD), of the deep flexional tendon of the finger (TFPD) or of its accessory ligament (LA-TFPD), or still of the inter-bone muscle III, which are illustrated on FIG. 1.

Thus, the invention also relates to the application of the method for continuous measurement of the tension condition of a tendon as defined above, for the determination of the tension of an equine tendon when walking, trotting or galloping.

It also relates to a method to select a corrective iron fitting intended to modify the tension of a tendon in an equine, said method comprising the following steps:
 a) implementing the method for continuous measurement of the tension or galloping.

It also relates to a method to select a corrective iron fitting intended to modify the tension of a tendon in an equine, said method comprising the following steps:
 a) implementing the method for continuous measurement of the tension condition of a tendon, above on said tendon, after fitting the equines with a corrective iron fitting;
 b) selecting the corrective iron fitting in order to modify the tension condition of the tendon.

By << modifying >> the tension condition of the tendon is meant to increase or to reduce the tension condition according to the specific objects which are required.

Preferably, the stage step a) of the selecting method above is carried out successively with a plurality of corrective iron fittings, thereby enabling to select the most appropriate corrective iron fitting taking into account the objects of relieving of the tension load tracked.

The invention is further illustrated, without being limited thereto, by the following Figures and examples.

DESCRIPTION OF THE FIGURES

FIG. 2 illustrates the influence of the angle between the transmitter and the receiver on the ultrasonic signal recorded. FIG. 2a exhibits the angle convention used. The inter-transducer angle α corresponds to the angle formed by the two transducers placed symmetrically with respect to the normal at the skin. FIGS. 2b, 2c and 2d show the ultrasound signals collected for an inter-transducer angle respectively of α=40°, α=80° and α=110°. The axis of abscissae represents the time, expressed in microseconds. The axis of ordinates represents the amplitude of the signal recorded by the receiver, expressed in millivolts.

FIG. 3 illustrates four of the five experimental conditions presented in this document.

FIG. 6 illustrates the evolution of the ultrasonic signal collected by the receiver relative to the compression load exerted on an entire limb. FIGS. 6A, 6B, 6C and 6D show four examples of plots obtained respectively in the four experimental-conditions tested, i.e. skin intact (FIG. 6A), skin incised (FIG. 6B), skin withdrawn (FIG. 6C) and superficial flexional tendon of the acoustically isolated finger of the underlying anatomic formations. The different plots visible on these figures correspond to the ultrasound signals recorded for each load value expressed in kiloNewtons (kN). The axis of abscissae represents the time in microseconds and the axis of ordinates the amplitude of the signal in millivolts. The axis of ordinates has been dilated to facilitate the visual detection of the time of appearance of the first ultrasonic waves (materialised by a black vertical line on each Figure).

FIG. 8 is an illustrative diagram of a complete device enabling the implementation of the method for continuous measurement according to invention.

FIG. 9 illustrates the travel time of the ultrasounds between the transducer transmitter and the transducer receiver R5, after application of the device of FIG. 8 facing the tendon FSD of a horse.

At the time t=0, the horse has stopped. From the time t=2.4 seconds, the horse is walking. The dwarf bars on the axis of abscissae represent the moments when the fore limb is resting on the ground.

FIG. 10 illustrates the travel time of the ultrasounds between the transducer transmitter and the transducer receiver R5, after application of the device of FIG. 8 facing the Achilles' tendon in a man.

Figure 10A:
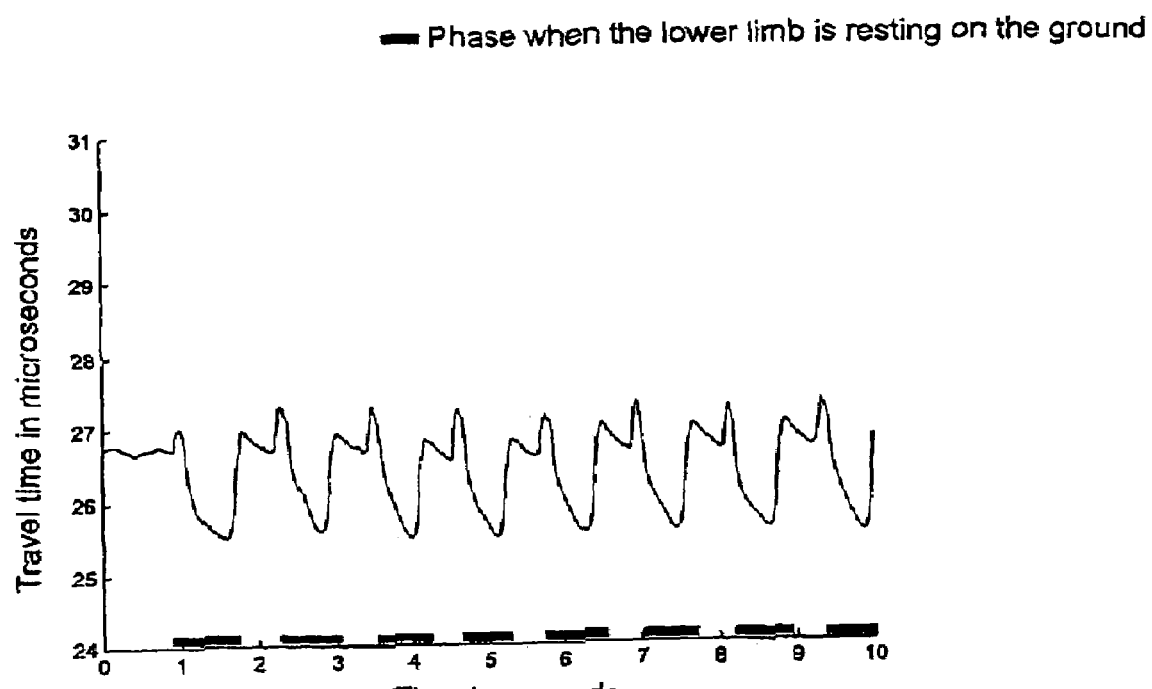
Figure 10B:
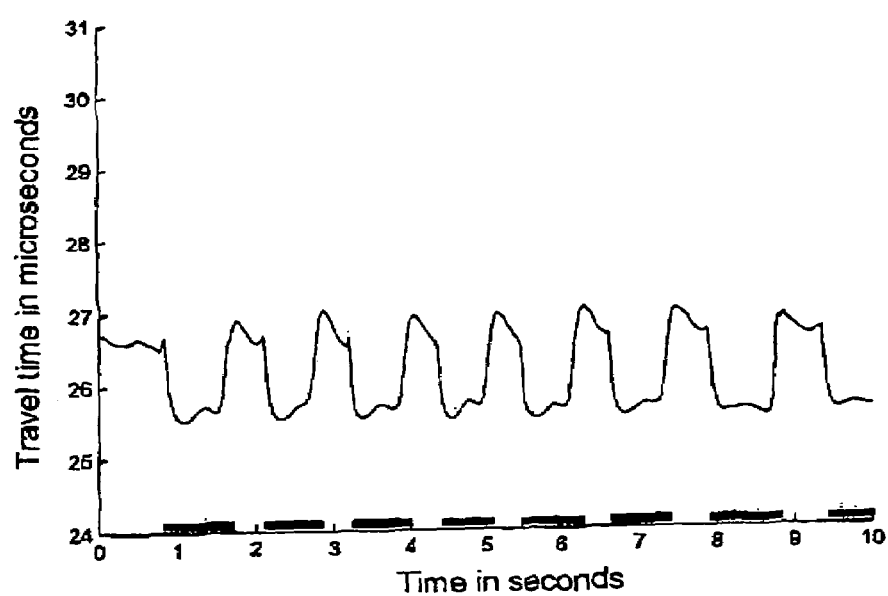

FIG. 10A: man walking; FIG. 10B: man going up the stairs.

The black bars on the axis of abscissae represent the moments when the lower limb are resting on the ground.

EXAMPLES

Example 1

Measurement of the Evolution of the Travel Time, of the Amplitude and of the Attenuation of an Ultrasonic Wave on an Isolated Tendon Subjected to Increasing Traction Loads a) Materials and Methods A.1 The Measurement Device The measuring device is composed of two ultrasound transducers (a transmitter and a receiver) connected to a box composed of electronic boards connected itself to a digital computer.

the transmitter and the receiver are cylindrical in shape, the vibrating element being, in both cases, a wide band (100%) disk of 12 mm in section, non focussed, around a central frequency of 1 MHz.

the box is composed of the following electronic boards:
a transmission board generating a wide band electric pulse at 200V, sent to the transmitter transducer,
a variable gain acquisition and amplification board (24 to 66 dB),
an analogue/digital conversion board ensuring on the one hand, the digitalisation of the reception signal amplified, and on the other hand, the interface with the digital computer for the transit of the controls and of the data.

the digital computer has a software for managing the whole instrumentation. This software provides:
the user interface,
the launch and the management of the measurements,
the storage of the data obtained.

Figure 3A:
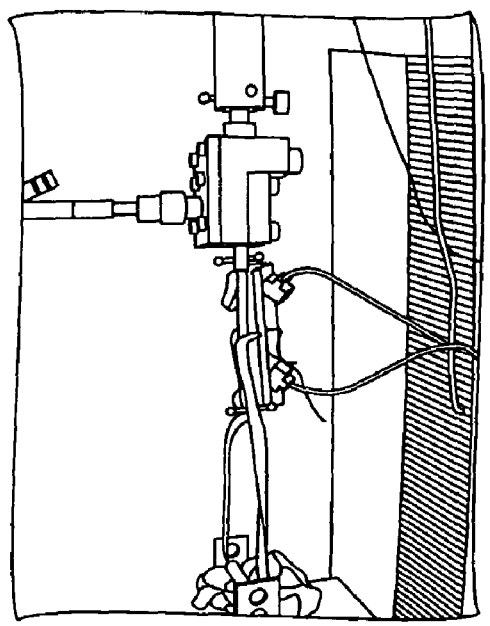
FIG. 3A shows a view of the experimental device shown below in example 1. The deep flexional tendon of the finger (TFPD) has been fixed proximally in a cryogenic claw and distally by its bone insertion on the distal phalange situated inside the shoe, then subjected to a tensile test between 0 and 5000 N.

Both transducers have been fixed on a contention system to the limb enabling to maintain it aligned according to the main axis of the tendon (FIG. 3A). In order to ensure good acoustic contact with the skin, an aqueous gel has been used as an ultrasound coupling. The ultrasounds have then been transmitted then collected once they have propagated in the tendon.

Figure 1:
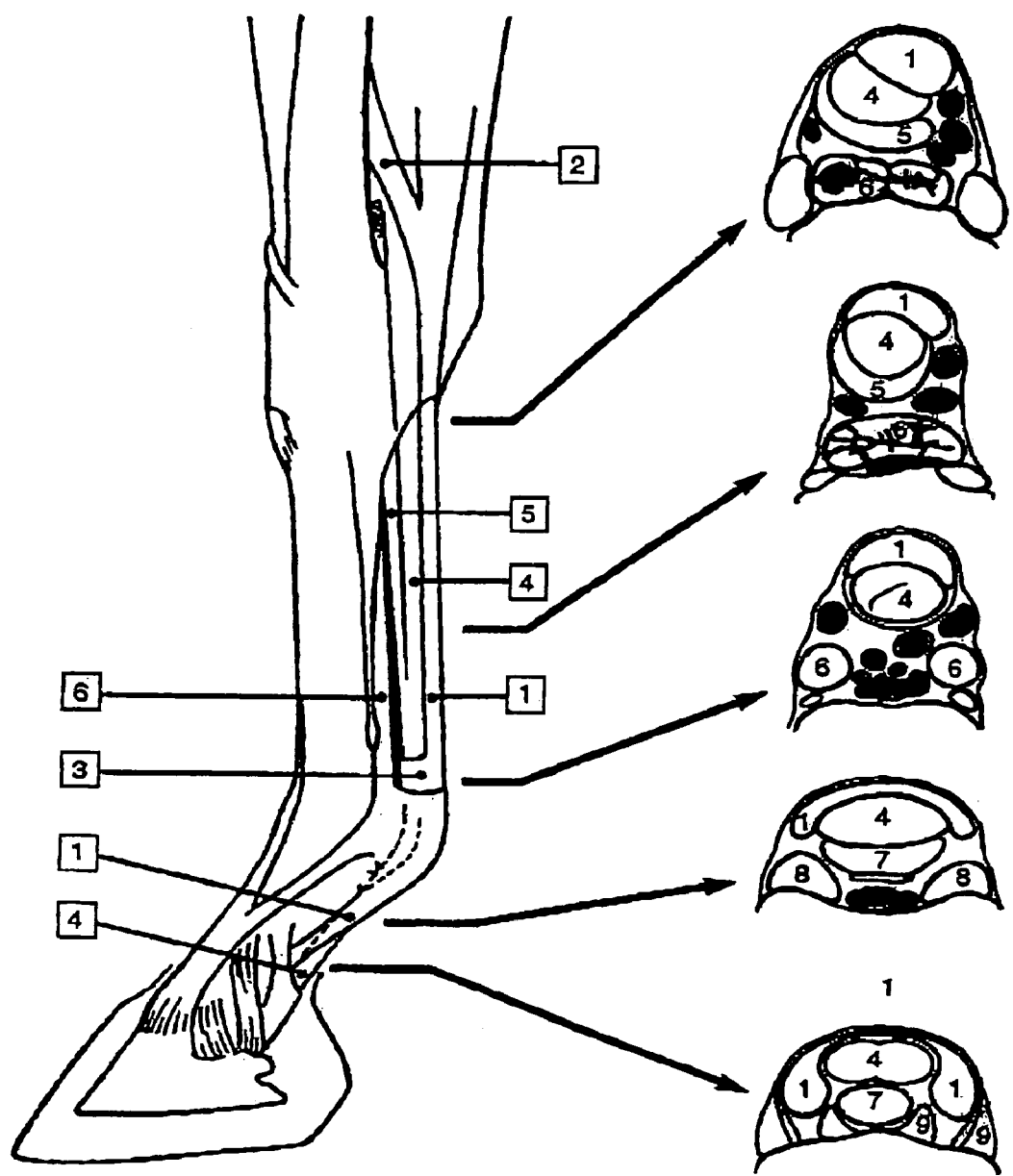
FIG. 1 represents schematically the muscular-tendinous apparatus of the hand of the horse.
 1) Superficial flexional tendon of the finger (TFSD).
 2) Accessory ligament of the TFSD (LA-TFSD).
 3) Manica flexoria.
 4) Deep flexional tendon of the finger (TFPD).
 5) Accessory ligament of the TFPD (LA-TFPD).
 6) Inter-bone muscle III.
 7) Right-hand sesamoid ligament (superficial plane).
 8) Oblique sesamoid ligaments (average plane).
 9) Palmar ligaments of the proximal interphalangeal joint.

More specifically, both transducers attached to the contention system have been placed on the palmar face of a deep flexional tendon of the finger (TFPD) of a horse, after the latter has been isolated from its limb. The TFPD is designated by the reference (4) on FIG. 1.

The TFPD has been subjected to a traction test of 0 to 5000 N. The tendon has been attached proximally in a cryogenic claw and distally by its bone insertion on the distal phalange situated inside the shoe.

b) Results

B.1 Influence of the Angle Formed by the Transducers on the Ultrasonic Signal

The influence of the angle formed by the transmitter and the receiver on the amplitude of the ultrasonic signal as the latter sets on, has been studied. This study has been realised by varying the inter-transducer angle α (see FIG. 2A) from 0° to 110° by 10° increments. The results obtained for an angle α de 40°, 80° and 110° are illustrated on FIGS. 2B, 2C and 2D. The results of this study have shown that although the signal was detected regardless of the value of the angle, the maximum amplitude of the signal, in particular as it appears, has been obtained for an inter-transducer angle of 80°.

Consequently, the remaining experimentations presented in the examples have been realised with an angle of 80° between the transmitter and the receiver.

Figure 4A:
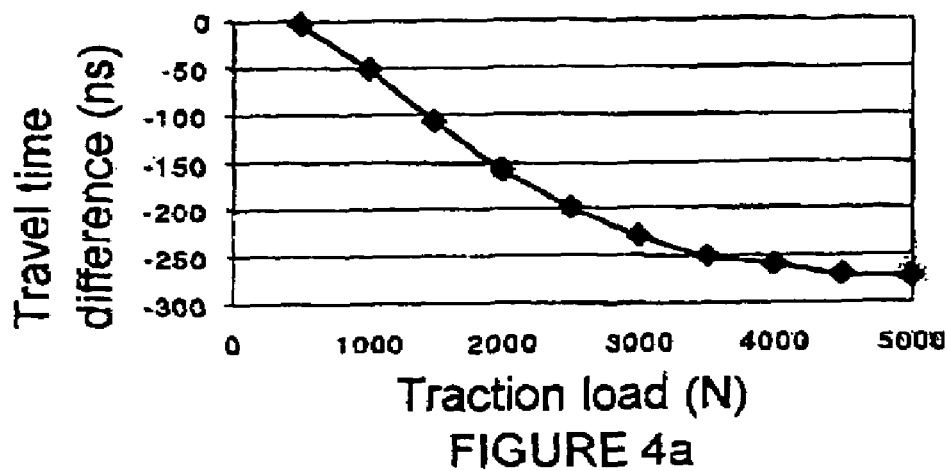
FIG. 4 illustrates the evolution of the travel time (FIG. 4A), of the amplitude (FIG. 4B), and of the attenuation (FIG. 4C) of the ultrasounds relative to the traction load exerted on an isolated tendon FPD. The axis of abscissae represents the traction load exerted on the tendon FPD, expressed in Newtons (N). The axis of ordinates represents the variation in travel time of the ultrasonic signal expressed in nanoseconds (ns) (FIG. 4A), the amplitude of the signal expressed in millivolts (mV) (FIG. 4B) and its attenuation expressed in decibels per megahertz (dB/MHz) (FIG. 4C).
Figure 4B:
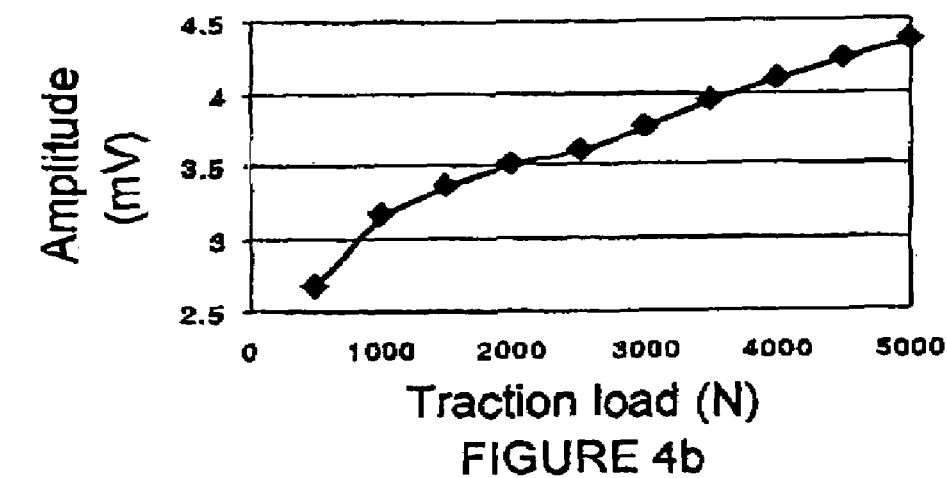
Figure 4C:
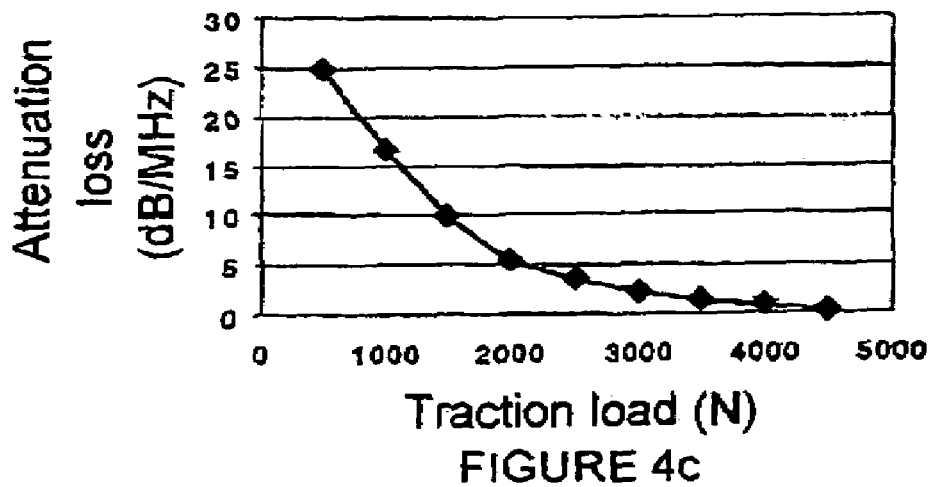

B.2 Measurement of the Variations of Travel Time, of Amplitude and of Attenuation of the Ultrasounds Relative to the Traction Load Applied to the Tendon As illustrated on FIG. 4, the travel time (FIG. 4A) and the attenuation (FIG. 4C) of the ultrasounds in the tendinous tissue diminish as the traction load exerted on the tendon increases. Conversely, the amplitude (FIG. 4B) of the ultrasonic signal increases with the traction load.

Thus, for a traction of 1000 N, the values of variation in travel time (variation with respect to the travel time observed at 500 N), in amplitude and in attenuation are respectively −54 ns, 3.16 mV and 24.56 dB/MHz whereas for a traction of 4000 N, these variables are respectively −262 ns, 4.08 mV and 0.69 dB/MHz.

Example 2

Measurement of the Evolution of the Travel Time, of the Amplitude and of the Attenuation of an Ultrasonic Wave on the Superficial Flexional Tendon of the Finger of a Complete Limb Subjected to Increasing Compression Loads.

A. Materials and Methods

A.1 The Measuring Device

The measuring device complies with that described for example 1.

For a test over a complete limb, the fore limb of a horse has been isolated at the distal third of the humerus, then has been subjected to a compression load varying from 0 to 6000 N. The compression of the limb will impose a traction load to the three tendons of the limb. The measuring device has been applied to the palmar face of the medium metacarpian region of the limb, en regard of the superficial flexional tendon of the finger (TFSD), referred (1) in FIG. 1.

Figure 3B:
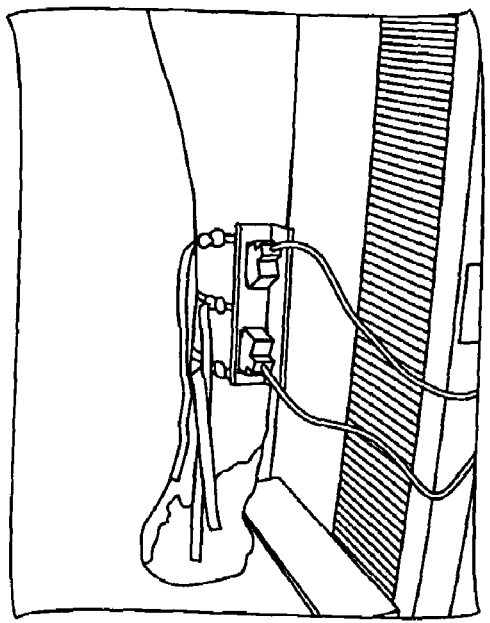
FIGS. 3B, 3C and 3D illustrate respectively the experiments a) (intact skin), c) (skin withdrawn) and d) (skin withdrawn and TFSD insulated acoustically of the underlying formations). On these 4 illustrations one distinguishes both transducers (in black) mounted on the contention system (in light grey) which enables to maintain it aligned according to the main axis of the tendon and to impose thereto a predetermined angle with respect to the latter.
Figure 3C:
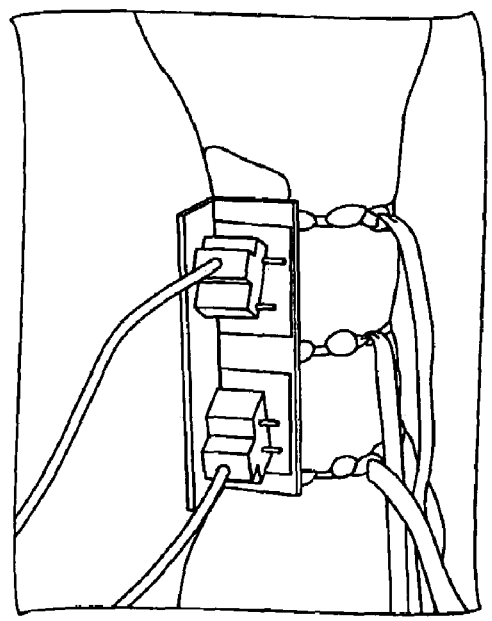
Figure 3D:
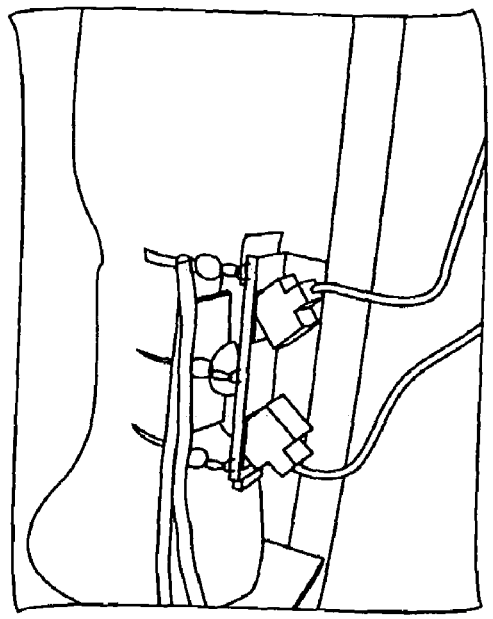

Four conditions have been tested successively:
a) Shaved skin intact (FIG. 3B);
b) Skin incised between both transducers;
c) Skin withdrawn (FIG. 3C); and
d) TFSD insulated acoustically from the underlying structures (other tendons and metacarpian bones) by dint of a sheet of paper inserted between the TFSD and the TFPD (FIG. 3D).

B. Results

In the tests of the example 2 on the entire limb, the flexional tendons of the finger have been stretched gradually as the compression force of the limb increases.

Figure 5A:
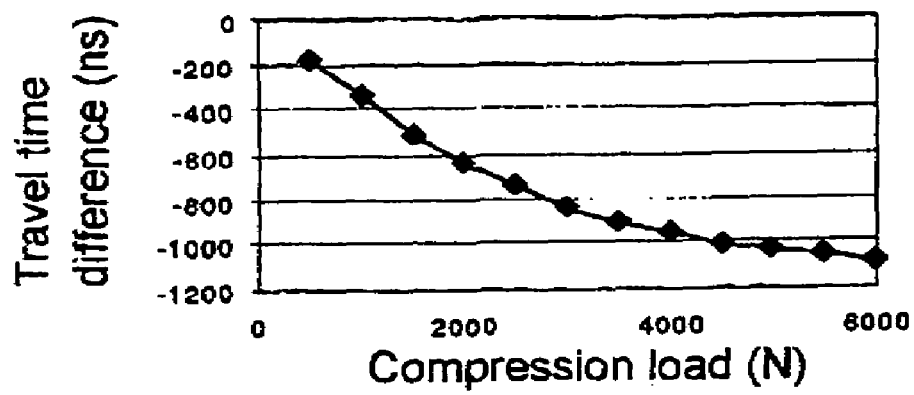
FIG. 5 illustrates the evolution of the travel time (FIG. 5A), of the amplitude (FIG. 5B) and of the attenuation (FIG. 5C) of the ultrasounds relative to the force of compression exerted on an entire limb, the transducers being arranged on the skin facing the tendon FSD, the skin being shaved and intact. The axis of abscissae represents the compression load exerted on the limb, expressed in Newtons (N). The axis of ordinates represents the variation in travel time of the ultrasound signal, expressed in nanoseconds (ns) (FIG. 5A), the amplitude of the signal expressed in millivolts (mV) (FIG. 5B) and its attenuation expressed in decibels per megahertz (dB/MHz) (FIG. 5C).
Figure 5B:
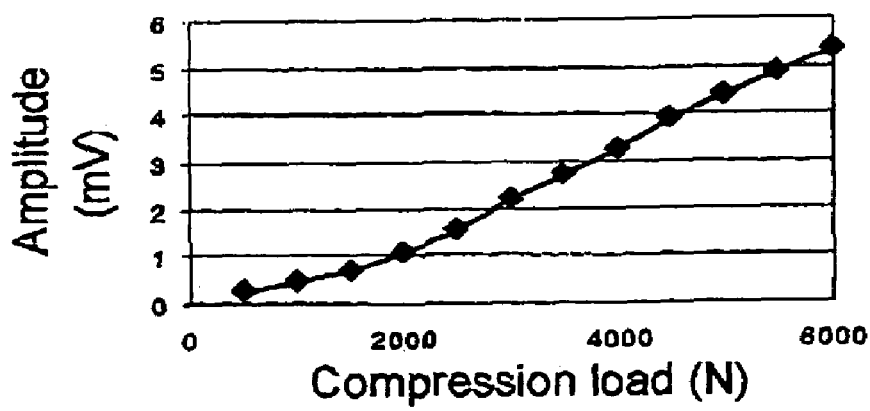
Figure 5C:
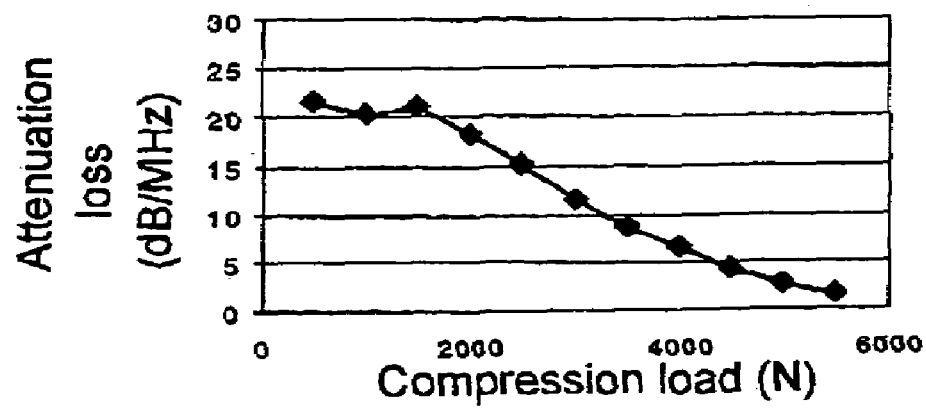

As observed on the example 1, the greater the compression load exerted on the entire limb, i.e. the greater the traction load imposed to the tendons, and the smaller the travel time (FIG. 5A) and the attenuation (FIG. 5C) of the ultrasounds and, conversely, the greater the amplitude (FIG. 5B) of the ultrasonic signal. These observations are valid regardless of the experimental condition (skin intact, incised, withdrawn or TFSD Insulated acoustically).

The comparison of the average travel times measured in these 4 experimental conditions (vertical lines of FIG. 6) shows that in the presence of the skin, intact or incised, the time taken by the ultrasounds to reach the receiver is longer by 1.25 microsecond that when the skin is withdrawn.

Considering that the propagation speed of the ultrasounds in the skin is 1500 m/s, this delay corresponds to a skin thickness of approximately 1 mm, which is perfectly coherent with the anatomic data.

Besides, no significant difference of this average travel time has been observed between the condition c) (skin withdrawn) and the condition d) (skin withdrawn and TFSD insulated acoustically from the underlying formations).

One may therefore conclude from both these observations that the first ultrasounds received by the receiver have been circulated through the most superficial tendon (TFSD) and not through the skin or other anatomic formations.

Example 3

Figures 7A, 7B:
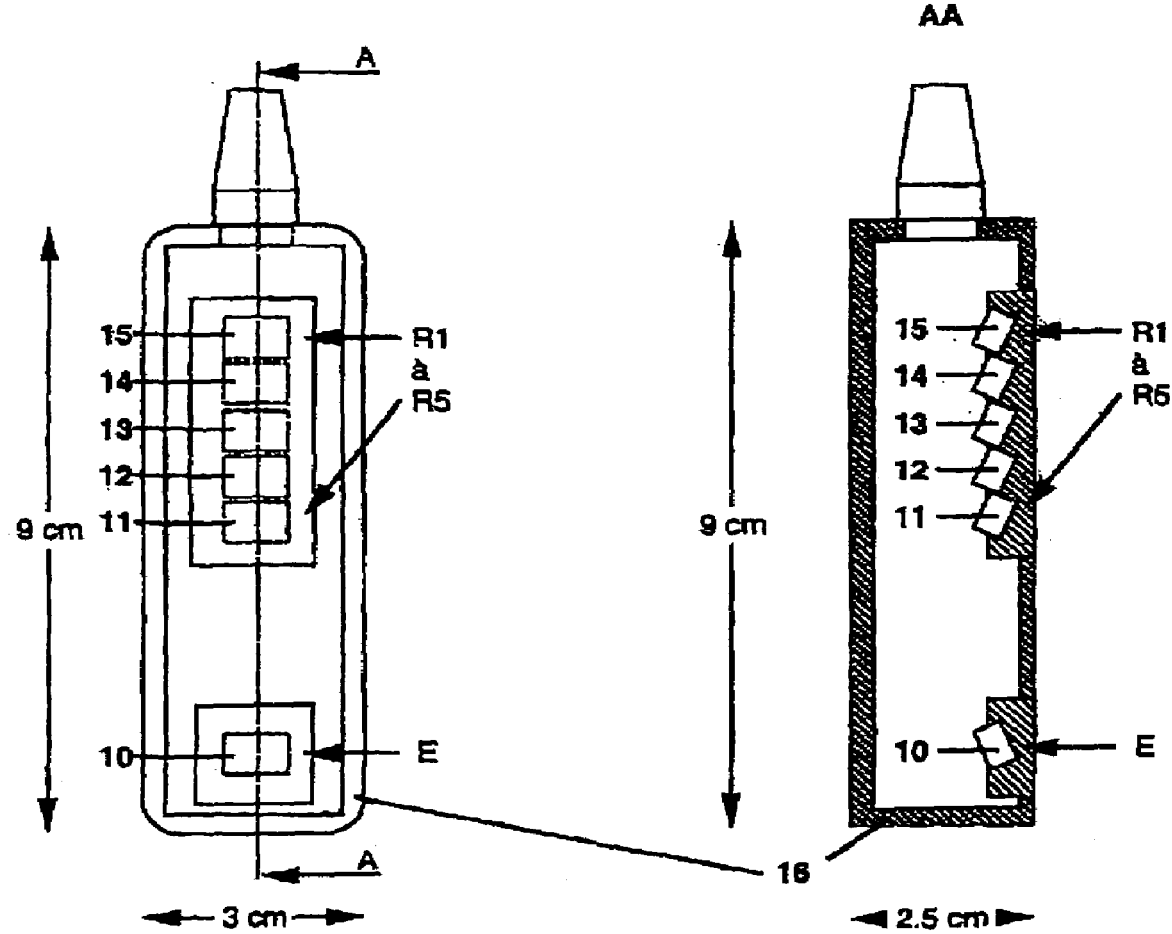
FIG. 7A is a top view of the transducer comprising a transmitter and 5 receivers.
FIG. 7B represents a longitudinal cross section of the transducer and FIG. 7C a side view (10) is the ultrasound transmitter; (11) to (15) represent respectively the ultrasound receivers R1 to R5.
Figure 7C:
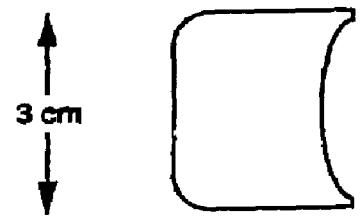
FIG. 7 is the diagram of a transducer enabling the implementation of the method according to the invention.

A Measuring Device Usable in the Implementation of the Method According to Invention As illustrated on FIG. 7B, the transmitter (10) on the one hand and the receivers (11 to 15) on the other hand, form an angle selected in order to optimise the amplitude of the ultrasonic signal recorded. The transducer is connected with an electronic box for controlling, processing and storing the signal.

FIG. 8 illustrates an embodiment representative of the equipment fitting a horse with a complete device for measuring the tension condition of a tendon, of a ligament or of a muscle for the implementation of the method according to invention.

Figure 8A:
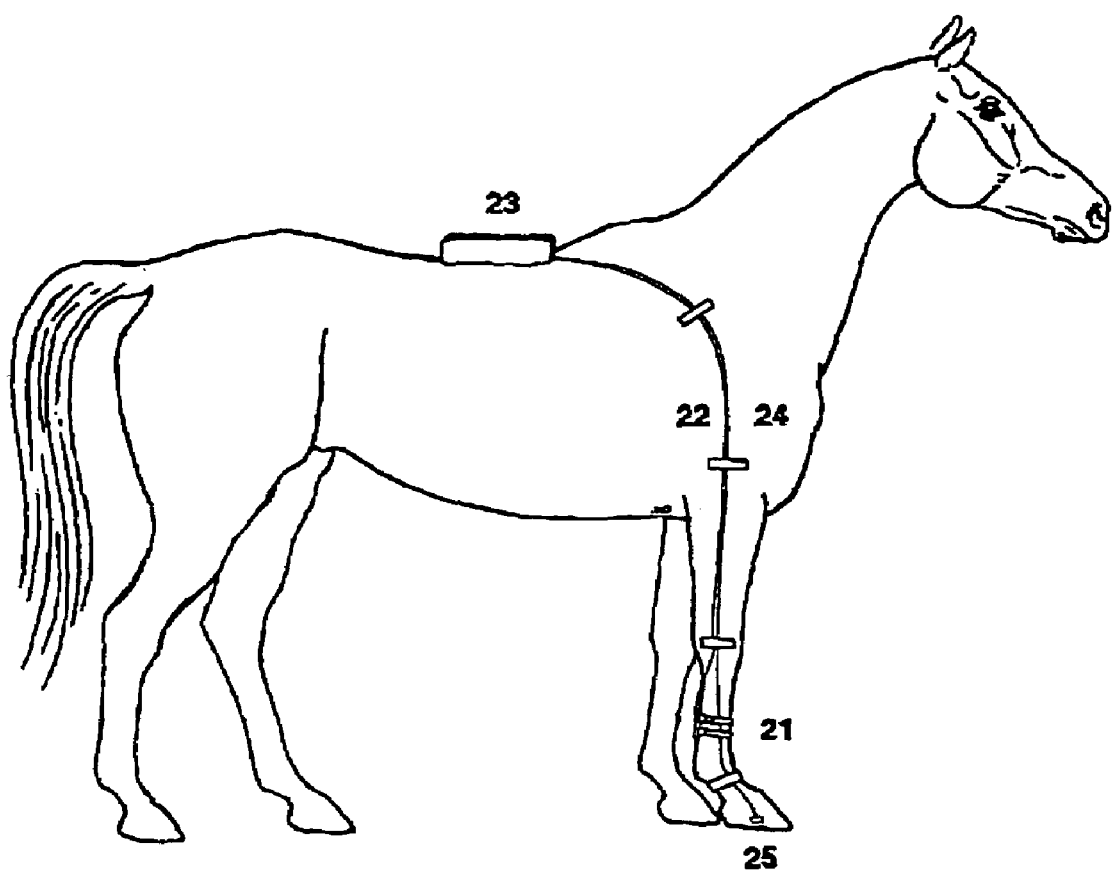
FIG. 8A represents the transducer (21) and its contention system on the limb.

FIG. 8A represents the contention device of the transducer (21) enabling to maintain, using straps, the transducer facing the tendon, the ligament or the muscle investigated.

Figure 8B:
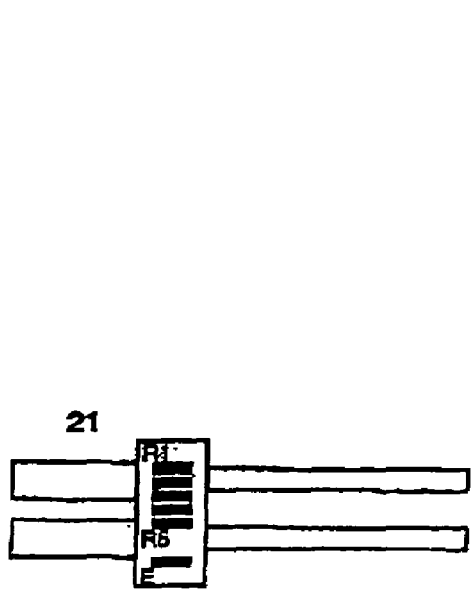
FIG. 8B represents the detail of a fore limb of a horse whereon has been fixed the transducer (21) using the contention system illustrated on FIG. 8A and an accelerometer (25) enabling the detection when the limb is resting and is taking off during the movement. The transducer (21) and the accelerometer (25) are linked with a measurement recording device by dint of the electrical or optical cables (22) and (24).

FIG. 8B illustrates the fore limb of a horse equipped with the device (21) from which runs an electric cable (22) enabling the transmission of the controls for transmitting ultrasounds and receiving ultrasound signals collected by the receivers.

In the embodiment of FIG. 8B, the system also comprises an accelerometer (25) from which runs a cable (24) for transmitting the accelerometer signal.

Figure 8C:
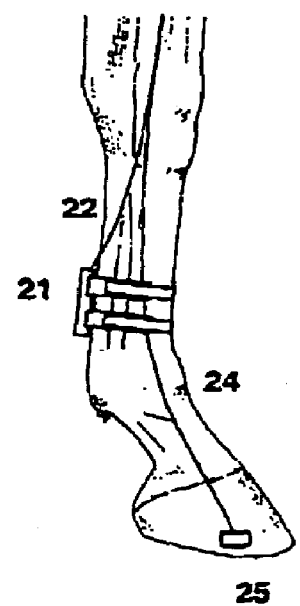
FIG. 8C is an overview of the complete device fitting a horse. The transducer (21) and the accelerometer (25) are connected to a box (23) attached to the back of the animal. This box (23) contains the control electronics of the transducer, the processing electronics of the ultrasound signals and the storage system of the information.

FIG. 8C illustrates an overview of a horse equipped with the measuring complete device, which also comprises an electronic box (23) for controlling and processing the signal and which also comprises means for storing the information issued from the transducers (21) and (25).

Example 4

Travel Time of an Ultrasonic Wave, Measured Facing the Superficial Flexional Tendon of the Finger of a Horse Walking and Trotting a) Materials and Methods:

A.1 Measuring Device

The horse has been equipped with the measuring device described in the example 3. As illustrated on the FIGS. 8B and 8C, the electronics have been attached to the back of the animal and the accelerometer on its right-hand shoe. The ultrasound transducer has been arranged facing the tendon FSD, against the skin of the medium metacarpian region of the right-hand fore limb.

A.2 Records

Two 10-second records, the one when walking, the other when trotting, have been made. In both cases, the record has been triggered, the horse being held in hand when immobile.

After approximately one second recording, the animal has been led, straight ahead and on a hard ground, on the one hand on a walking pace and, on the other hand, gradually on a trotting pace.

A.3 Processing the Records

To calculate the travel time of the ultrasonic wave, the signals recorded have been processed according to the procedure set forth in the present description. To determine the periods corresponding to the phase when the limb is resting on the ground and to the back-up phase, the acceleration peaks caused by the shoe landing and taking off have been identified on the accelerometer signal.

b) Results

Figure 9A:
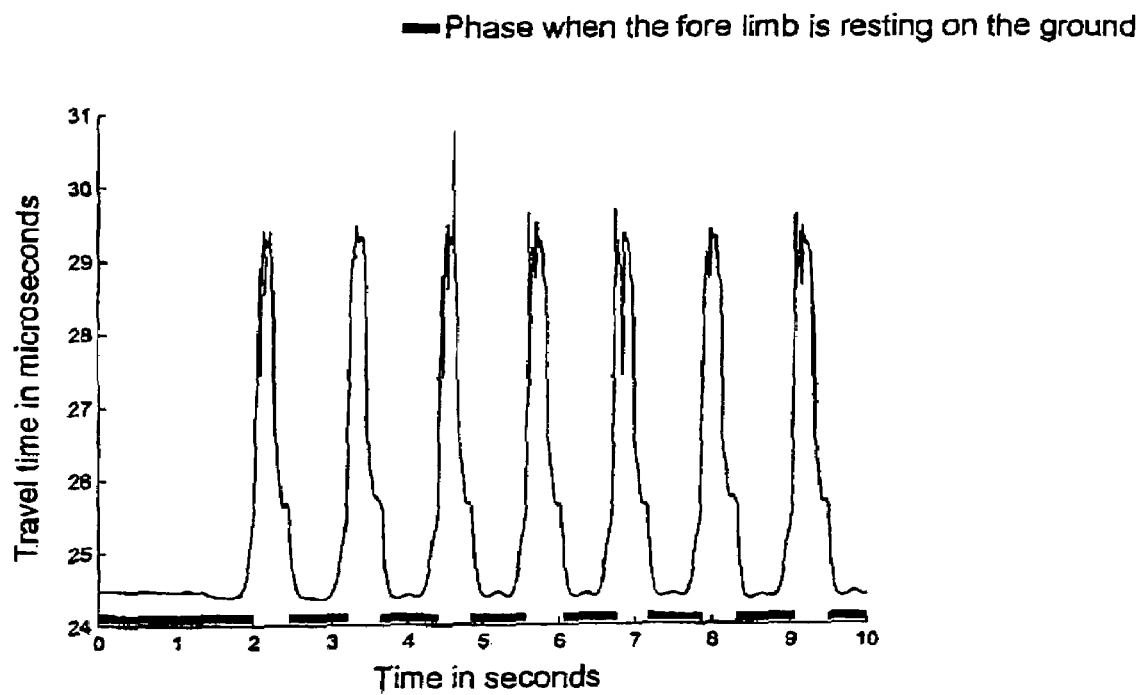
FIG. 9A: horse walking.
Figure 9B:
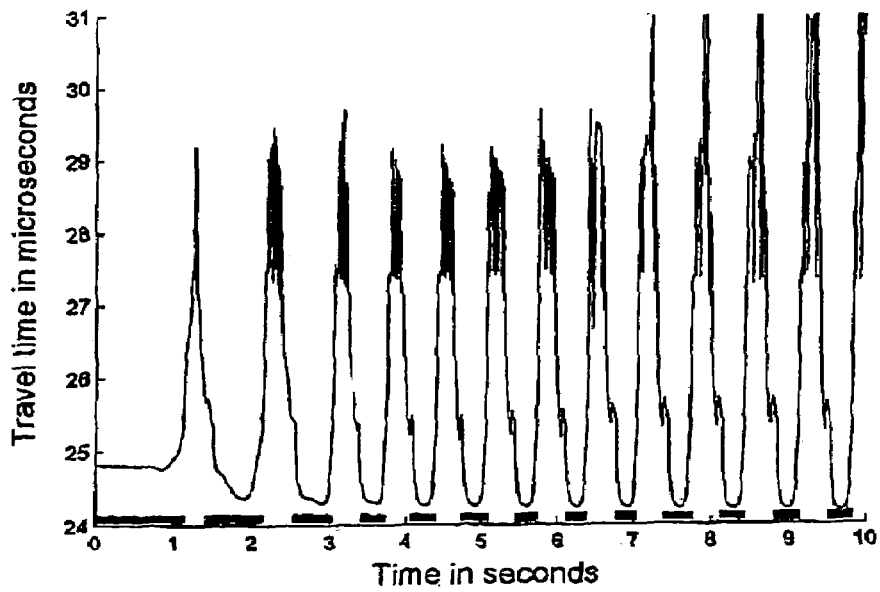
FIG. 9B: horse trotting.

FIGS. 9A and 9B show the travel time of the ultrasonic wave, obtained on the receiver R5, respectively when walking and when trotting. For exemplification purposes, one may quote as results the minimum travel times observed when walking and when trotting for the last five strides (i.e. after stabilisation of the horse's speed). They were, respectively when walking and when trotting, 24.37±0.02 $\mu$s and 24.20±0.02 $\mu$s.

These results show clearly that the value of the travel time of the ultrasonic wave, between an ultrasound transmitter and an ultrasound receiver localised at a fixed predetermined distance from the transmitter, is reversely proportional to the tension load of the tendon of the horse.

Example 5

Travel Time of an Ultrasonic Wave, Measured Facing the Achilles' Tendon of a Man Walking and Going Up the Stairs.

a) Materials and Methods:

A.1 Measuring Device

The measuring device is identical to that described in the examples 3 and 4. The subject has been equipped with a rucksack wherein the electronics have been placed. The accelerometer has been attached to the right-hand heel of the subject and the ultrasound transducer has been arranged, transmitter downwards, against the skin facing its right-hand Achilles' tendon.

A.2 Records

Two 10-second records, the one walking on a straight line, the other when going up several flights of steps, have been carried out. Contrary to the previous example, the record has been triggered as right-hand lower limb of the subject was in back-up phase (or pendulum phase).

A.3 Processing the Records

To calculate the travel time of the ultrasonic wave, the signals recorded have been processed according to the procedure set forth in the present description. To determine the periods corresponding to the phase when the limb is resting on the ground and to the back-up phase, the acceleration peaks caused by the limb landing and taking off have been identified on the accelerometer signal.

b) Results:

FIGS. 10A and 10B show the travel time of the ultrasonic wave obtained on the receiver R5, respectively when walking and going up the stairs. To exemplify the results, the average travel time observed on 7 walking strides was 26.38±0.54 $\mu$s against 26.13±0.56 $\mu$s for 7 successive upstairs climbings.

These results show clearly that the value of the travel time of the ultrasonic wave, between an ultrasound transmitter and an ultrasound receiver localised at a fixed predetermined distance from the transmitter, is reversely proportional to the tension load of the human tendon.

What is claimed is:

1. A method for determining the tension condition of a material at a given time, comprising the steps of:
   (a) propagating an ultrasonic wave transmitted in a material between an ultrasound source and at least one ultrasound receiver situated at a fixed predetermined distance from the ultrasound source, wherein the material is under a tension condition; and
   (b) after propagation of the ultrasonic wave, extracting at least one parameter from the ultrasonic wave and calculating its value, wherein the value of the at least one parameter varies with the tension condition of the material, said variation of the at least one parameter being directly proportional or inversely proportional to the variation in the tension condition of said material.

2. The method according to claim 1, wherein the at least one parameter calculated on the basis of the ultrasonic signal is selected from among the following parameters:
   (i) the travel time of the ultrasonic wave over a predetermined distance in said material;
   (ii) the amplitude of the ultrasonic wave at the reception point of the ultrasonic signal;
   (iii) the attenuation of the ultrasonic wave at the reception point of the ultrasonic signal;
   (iv) the average frequency of the ultrasonic wave at the reception point of the ultrasonic signal;
   (v) the maximum frequency of the ultrasonic wave at the reception point of the sound signal.

3. The method according to claim 1, wherein in the step of extracting and calculating, the values are calculated for at least one of the following parameter combinations:
   (i) the travel time and the amplitude of the ultrasonic wave;
   (ii) the travel time and the attenuation of the ultrasonic wave;
   (iii) the amplitude and the attenuation of the ultrasonic wave;
   (iv) the travel time, the amplitude and the attenuation of the ultrasonic wave.

4. The method according to claim 1, wherein the material to be tested is a biological material selected from among a tendon, a ligament and a muscle.

5. The method according to claim 1, wherein the frequency of ultrasounds transmitted by the source ranges between 15 KHz and 10 GHz.

6. A method for continuous measurement of the tension condition of a material, comprising implementing the method according to claim 1 for a plurality of time-spread, given instants.

7. A method for selection of a corrective iron fitting intended to modify the tension of a tendon in equines comprising the following steps:
   a) implementing the method according to claim 6 on said tendon, after fitting the equines with a corrective iron fitting, or successively with a plurality of corrective iron fittings;
   b) selecting the corrective iron fitting in order to modify the tension condition of the tendon.

8. A method for continuous measurement of the tension condition of a material, comprising implementing the method according to claim 1 for a plurality of time-spread, given instants at a sampling frequency greater than or equal to 2.5 times that of the frequency at which the tension condition evolves.

9. An application of the method according to claim 1 to the determination of the tension condition of a tendon, of a ligament or of a muscle in a man or an animal.

10. An application according to claim 9, wherein the determination of the tension of a tendon, of a ligament or of a muscle is carried out in a man or an animal in motion, during normal or pathological locomotion, during a sports action.

11. An application according to claim 9, wherein the method is carried out on damaged tissues or after fitting a limb with a prosthesis.

12. The method according to claim 1, further comprising the steps of:
  a) before the propagating step, applying an ultrasound source in contact with the material to be tested;
  b) between the propagating step and the extracting and calculating step, recording the signals from the ultrasound source using at least one receiver situated at a fixed predetermined distance from said source, the line connecting the source and the at least one receiver being parallel to the longitudinal axis of the material to be tested; and
  c) after the extracting and calculating step, determining the tension condition of the material by calculating the value of the at least one parameter extracted from the ultrasonic signal at a given time.

13. The method according to claim 12, wherein the ultrasound source and the ultrasound receivers are placed in contact with the material to be tested and aligned according to the main axis of said material.

14. The method according to claim 12, wherein the signals from the ultrasound source are recorded by a plurality of receivers situated at a predetermined distance relative to one another and with respect to the ultrasound source.

15. The method according to claim 12, wherein the ultrasound source, on the one hand, and the plurality of receivers, on the other hand, form between themselves an angle ranging between 0° and 180°.

16. The method according to claim 12, wherein the at least one parameter extracted from the ultrasonic signal received is calculated between at least two receivers.

17. The method according to claim 12, wherein the material to be tested is a biological material selected from among a tendon, a ligament and a muscle.

18. The method according to claim 17, wherein for a tendon, a ligament or a muscle, the line connecting the source and the at least one receiver is parallel to the axis along which are aligned respectively the tendinous, ligamentous or muscular fibres.

19. The method according to claim 12, wherein the ultrasound source, on the one hand, and the plurality of receivers, on the other hand, form between themselves an angle ranging between 60° and 100°.

20. The method according to claim 12, wherein the ultrasound source, on the one hand, and the plurality of receivers, on the other hand, form between themselves an angle of approximately 80°.

21. The method according to claim 1, wherein the frequency of ultrasounds transmitted by the source ranges between 20 KHz and 100 MHz.

22. The method according to claim 1, wherein the frequency of ultrasounds transmitted by the source ranges between 20 KHz and 50 MHz.

* * * * *

UNITED STATES PATENT AND TRADEMARK OFFICE
CERTIFICATE OF CORRECTION

PATENT NO. : 7,010,435 B2 Page 1 of 1
APPLICATION NO. : 10/492601
DATED : March 7, 2006
INVENTOR(S) : Philippe Pourcelot et al.

It is certified that error appears in the above-identified patent and that said Letters Patent is hereby corrected as shown below:

On the title page of the patent:
Insert Item [73],
Assignee: INSTITUT NATIONAL DE LA RECHERCHE ARGONOMIQUE (INRA), Paris Cedex (FR)

-- ECOLE NATIONAL VETERINAIRE D'ALFORT (ENVA), Maisons Alfort Cedex, (FR) --

Signed and Sealed this

Fifth Day of December, 2006

JON W. DUDAS
*Director of the United States Patent and Trademark Office*